(12) United States Patent
Zhang et al.

(10) Patent No.: US 8,420,652 B2
(45) Date of Patent: Apr. 16, 2013

(54) USE OF ARYL PIPERAZINE DERIVATIVES IN MANUFACTURING MEDICANTS FOR TREATING PAIN

(75) Inventors: Guisen Zhang, Xuzhou (CN); Lin Guo, Xuzhou (CN); Xiangping Yang, Xuzhou (CN); Xiangqing Xu, Xuzhou (CN); Jianqi Li, Xuzhou (CN); Guan Wang, Xuzhou (CN); Yanqin Ma, Xuzhou (CN); Shuming Hu, Xuzhou (CN); Shicheng Liu, Xuzhou (CN); Shixia Zhou, Xuzhou (CN)

(73) Assignee: NHWA Pharma Corporation (CN)

( * ) Notice: Subject to any disclaimer, the term of this patent is extended or adjusted under 35 U.S.C. 154(b) by 334 days.

(21) Appl. No.: 12/865,599

(22) PCT Filed: Jan. 15, 2009

(86) PCT No.: PCT/CN2009/070162
§ 371 (c)(1),
(2), (4) Date: Jul. 30, 2010

(87) PCT Pub. No.: WO2009/097774
PCT Pub. Date: Aug. 13, 2009

(65) Prior Publication Data
US 2010/0331340 A1 Dec. 30, 2010

(30) Foreign Application Priority Data
Jan. 31, 2008 (CN) .......................... 2008 1 0018896

(51) Int. Cl.
*A61K 31/497* (2006.01)
*A61K 31/00* (2006.01)
*A01N 43/00* (2006.01)

(52) U.S. Cl.
USPC ................................. 514/252.12; 514/211.01

(58) Field of Classification Search ............. 514/252.12
See application file for complete search history.

(56) References Cited

U.S. PATENT DOCUMENTS
5,369,103 A    11/1994   Cliffe et al.

FOREIGN PATENT DOCUMENTS
| EP | 1123926 | 8/2001 |
| EP | 1627871 | 2/2006 |
| WO | WO 2007/071055 A1 | 6/2007 |
| WO | WO 2007/104783 A2 | 9/2007 |

OTHER PUBLICATIONS

Supplemental European Search Report for corresponding European application No. EP 09709122, date of mailing Dec. 9, 2010.
International Search Report for corresponding PCT application No. PCT/CN2009/070162, date of mailing Apr. 30, 2009.

*Primary Examiner* — Sreeni Padmanabhan
*Assistant Examiner* — Layla Soroush
(74) *Attorney, Agent, or Firm* — Myers Bigel Sibley & Sajovec, PA

(57) ABSTRACT

The use of aryl piperazines of formula (I) in manufacturing a medicament for treating acute pain, neuropathic pain or receptive nociceptive pain in mammals including human beings is disclosed.

(I)

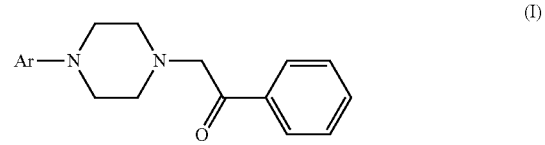

3 Claims, No Drawings

USE OF ARYL PIPERAZINE DERIVATIVES IN MANUFACTURING MEDICANTS FOR TREATING PAIN

CROSS REFERENCE TO RELATED APPLICATION

This application is a 35 U.S.C. §371 national phase application of PCT Application No. PCT/CN2009/070162, filed on Jan. 15, 2009, which claims priority from Chinese Patent Application 200810018896.0, filed on Jan. 31, 2008, the disclosures and contents of which are hereby incorporated by reference as if recited in full herein. The above-referenced PCT International Application was published in Chinese as International Publication No. WO 2009/097774 A1.

FIELD OF THE INVENTION

The invention relates to use of aryl piperazine derivatives and pharmaceutically acceptable salt thereof alone or in combination with other analgesics in manufacturing a medicament for treating acute pain, neuropathic pain or receptive nociceptive pain in mammals including human beings.

BACKGROUND OF THE INVENTION

EP1627871 discloses a compound of the following formula, which may be used as an intermediate to prepare a steroid hormone sulfatase inhibitor:

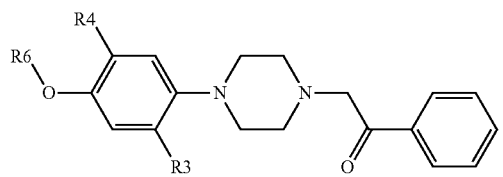

wherein R3 and R4 each represents hydrogen, halogen, cyano, or lower alkyl; R6 represents hydrogen or a protecting group of hydroxyl. The publication does not describe the pharmacological activity of the compound of the above formula.

EP1123926 discloses a compound of the following formula, which can be used as an intermediate to produce piperazine derivatives for treatment of central nervous system dysfunction:

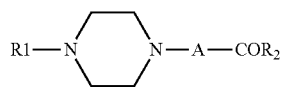

wherein R1 is monocyclic or dicyclic aryl or heteroaryl; R2 is aryl or heteroaryl; A is $CH_2$ or —$CH_2CH_2$—. The publication does not describe the pharmacological activity of the compound of the above formula.

It is discovered that the compound of the following formula (I) and pharmaceutically acceptable salt thereof may be used alone or in combination with other analgesics (in this case synergetic effect can occur) for treating acute pain, neuropathic pain or receptive nociceptive pain in mammals including human beings.

SUMMARY OF THE INVENTION

The invention provides the use of aryl piperazine derivatives of formula (I) or a pharmaceutically acceptable salt thereof alone or in combination with other analgesics in manufacturing a medicament for treating acute pain, neuropathic pain or receptive nociceptive pain in mammals including human beings:

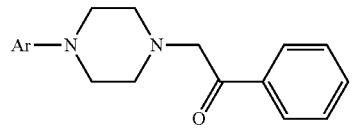

wherein Ar is aryl or heteroaryl which is unsubstituted or substituted by a group selected from the group consisting of halogen, $C_{1-6}$alkyl, $C_{1-4}$alkoxyl and halogenated $C_{1-4}$alkyl.

Another aspect of the invention provides methods for treating acute pain, neuropathic pain or receptive nociceptive pain in mammals including human beings with the compound of formula (I), comprising administration of a therapeutically effective amount of the compound to a subject in need of such treatment.

DETAILED DESCRIPTION OF THE EMBODIMENTS

As used herein, halogen refers to F, Cl, Br or I. In some embodiments, halogen refers to F, Cl or Br.

$C_{1-6}$ alkyl means a linear, branched or cyclic saturated alkyl containing 1, 2, 3, 4, 5 or 6 carbon atoms, such as methyl, ethyl, propyl, isopropyl, n-butyl, n-pentyl, and n-hexyl. In one embodiment, methyl is preferred.

$C_{1-4}$ alkoxyl means an alkyl-O— group, wherein the alkyl is an alkyl containing 1, 2, 3 or 4 carbon atoms as defined above, such as methoxyl, ethoxyl, n-propoxyl, iso-propoxyl and n-Butoxyl. In one embodiment, methoxyl is preferred.

Halogenated $C_{1-4}$ alkyl means an alkyl containing 1, 2, 3 or 4 carbon atoms as defined above which is substituted partly or completely by halogen. In one embodiment, trifluoromethyl is preferred.

Aryl means an aliphatic aromatic group containing 5-14 carbon atoms, such as phenyl or naphthyl. In one embodiment, phenyl is preferred. In another embodiment, phenyl substituted with substitutents described herein is preferred.

Heteroaryl means a monocyclic or bicyclic 5-14 member aryl containing 1-4 heteroatoms selected from O, N and S. In some embodiments, heteroaryl containing 1 or 2 heteroatoms selected from O, N and S is preferred. In another embodiment, benzothiazolyl, pyridyl or pyrimidinyl is preferred.

In one embodiment, the aryl is mono- or di-substituted phenyl, wherein the substituent is selected from F, Cl, Br, methyl, methoxyl or trifluoromethyl.

In another embodiment, the heteroaryl refers to benzothiazolyl, pyridyl or pyrimidinyl, and the substituted heteroaryl comprises no more than two substituents selected from F, Cl, Br, methyl, methoxyl or trifluoromethyl.

The compound of formula (I) may be prepared in the form of pharmaceutically acceptable salts according to common methods known to one skilled in the art. The pharmaceutically acceptable salts are those conventionally used in the art, such as acid addition salts. The pharmaceutically acceptable acid addition salts include inorganic acid addition salts made from inorganic acids such as hydrochloric acid, hydrobromic acid, phosphoric acid or sulfuric acid; organic acid addition salts made from organic acids such as acetic acid, propionic acid, lactic acid, citric acid, fumaric acid, malic acid, succinic acid, salicylic acid, maleic acid, glycerophosphoric acid, acetosalicylic acid, and alkyl or aryl sulfonic acid such as methanesulfonic acid, benzene sulfonic acid or toluene sulfonic acid.

The use of the compound of formula (I) or the pharmaceutically acceptable salts in manufacturing a medicament for treating pain refers to the use as an analgesic in clinic. The acute pain includes but not limited to headache, arthralgia, mascular tension or dysmenorrheal. The neuropathic pain includes, but is not limited to, chronic backache, postherpetic neuralgia, diabetic peripheral neuralgia, fibromyalgia, cancer-related pain, phantom limb pain, labour pains and/or opioid analgesics resistant neuralgia. The perceptive nociceptive pain includes, but is not limited to, postoperative pain, toothache, pain from surgery, and/or pain from serious burns.

The compounds of formula (I) can be formulated to a pharmaceutical composition according to a common standard pharmaceutical technique for administration of the compounds in the treatment. For example, the compounds of formula (I) may be dissolved in oil, propylene glycol or other solvents commonly used for preparing injections. Preferable carriers include, but are not limited to, a saline solution, polyethylene glycol, ethanol, vegetable oil, isopropyl myristate and the like. For topical administration, the compounds of the invention may be formulated into the form of ointment or cream.

The compounds of formula (I) may be dissolved, suspended or emulsified in an aqueous solution such as a conventional saline solution and 5% glucose solution, or a non-aqueous solution such as synthetic fatty glyceride, high fatty acids ester and propylene glycol, and thereby an injection is formulated. The composition of the present invention may comprise conventional additives, such as a solubilizing agent, an isotonizing agent, a suspending agent, an emulsifying agent, a stabilizing agent and a preservative.

The administrating dose of the compound of formula (I) may depend on factors such as the condition, the weight of patients, severity of the disease, the formulation of the medicament, as well as route and time of administration, but those skilled in the art may determine it properly. To obtain a preferable effect, however, the daily dosage of the compounds of the present invention may be 1-200 mg/kg (body weight), preferably 1-100 mg/kg (body weight), while the dose may be administrated once or in several times.

According to the administration method, the pharmaceutical composition of the present invention may contain 0.001-99 wt % of the compound of formula (I), preferably 0.01-60 wt %.

In one embodiment, the pharmaceutical composition may be administrated to mammals including rats, mice, domestic animals or human beings by various routes. Any administration route can be applied, such as oral, transdermal, parenteral, subcutaneous, nasal, intramuscular or intravenous administration.

According to another aspect of the invention, the compound of formula (I) may be applied together with another analgesics so as to obtain a synergetic effect, with a ratio there between being one part of the compound of formula (I) to 1-10 parts of the other analgesics. The other analgesics includes, but are not limited to, non-steroidal anti-inflammatory drugs such as aspirin and naproxen, narcotic analgesics such as morphine, dolantin and fentanyl.

The compound of formula (I) may be manufactured according to the following schee:

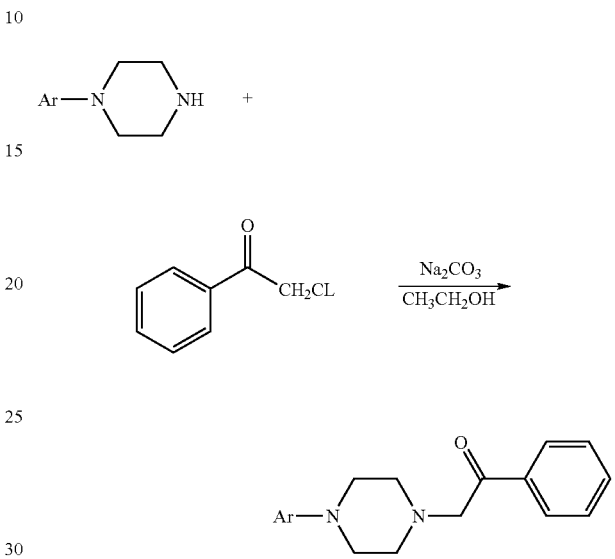

For example, 0.24 mol of a substituted aryl piperazine or heteroaryl piperazine, 0.24 mol of α-chloro acetophenone, 480 ml of ethanol, and 50.4 g of sodium carbonate are added to a 1000 ml flask with four necks. After the mixture is refluxed while stirring for 4 hours, the reaction is monitored with a thin-layer chromatography until the sample point of the principal product does not change any more, which indicates that the reaction is complete. After heat filtration, the filtrate is evaporated to dry, and the residue is dissolved with methylene chloride. The methylene chloride solution is washed with water until the pH is close to neutral. After dried with anhydrous sodium sulfate, the pH of the solution is adjusted to 3-4 with a saturated hydrogen chloride solution in ethyl acetate. The solid is filtrated, washed with ether, recrystallized with anhydrous ethanol, and then dried under vacuum at 50° C. An off-white solid is obtained.

EXAMPLES

The present invention is further explained by the following examples, but those skilled in the art can understand that the examples are only intended to explain the invention but should not be construed by way of limiting the scope of the present invention.

Preparation Examples

The compounds shown in the following Table 1 are prepared according the above conventional process from corresponding starting materials.

TABLE 1

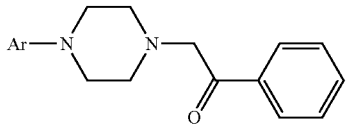

| Example | Ar | HMNR (300 MHz), δ (溶剂) | MS (m/z) |
|---|---|---|---|
| 1 | 2-methoxyl phenyl | 7.95 (d, J = 7.2, 2H), 7.72 (J = 7.2, 1H) 7.55 (J = 7.6, 2H), 7.16 (J = 7.6, 1H) 7.12 (d, J = 7.6, 1H), 7.05 (d, J = 7.6, 1H) 7.01 (J = 7.6, 1H), 5.00 (s, 1H) 3.82 (s, 3H), (CDCL$_3$) | 310.3$[M]^+$ 205.2$[C_{12}H_{17}N_2O]^+$ 105.1$[C_7H_5O]^+$ |
| 2 | 3-methoxyl phenyl | 8.01 (d, J = 7.6, 2H), 7.64 (J = 7.6, 1H) 7.53 (t, J = 7.6, 2H), 7.10 (t, J = 8.0, 1H) 6, 52 (dd, J = 2.0, 7.6, 1H), 6.44 (J = 2.0, 1H) 6.36 (dd, J = 2.0, 7.6, 1H), 3.88 (s, 2H), 3.71 (s, 3H ), (CDCL$_3$) | 310.3$[M]^+$ 205.2$[C_{12}H_{17}N_2O]^+$ 105.1$[C_7H_5O]^+$ |
| 3 | 4-methoxyl phenyl | 7.94 (d, J = 7.6, 2H), 7.72 (J = 7.6, 1H) 7.55 (J = 7.6, 2H), 7.12 (d, J = 8.8, 2H) 7.08 (d, J = 8.8, 2H), 5.00 (s, 2H) 3.76 (s, 3H), (CDCL$_3$) | 310.3$[M]^+$ 205.2$[C_{12}H_{17}N_2O]^+$ 105.1$[C_7H_5O]^+$ |
| 4 | 2-chloro phenyl | 8.02 (d, J = 7.6, 2H), 7.64 (t, J = 7.6, 1H) 7.53 (J = 7.6, 2H), 7.39 (dd, J = 1.2, 7.6, 1H) 7.28 (td, J = 1.2, 7.6, 1H), 7.16 (dd, J = 1.2, 7.6, 1H), 7.03 (td, J = 1.2, 7.6, 1H), 3.93 (s, 2H) (CDCL$_3$) | 314.1$[M]^+$ 209.0$[C_{12}H_{17}N_2CL]^+$ 105.1$[C_7H_5O]^+$ |
| 5 | 3-chloro phenyl | 8.01 (d, J = 7.6, 2H), 7.64 (J = 7.2, 1H) 7.53 (J = 8.0, 2H), 7.20 (J = 8.0, 1H) 6.93 (J = 2.0, 1H), 6.89 (dd, J = 1.2, 7.6, 1H) 6.77 (dd, J = 1.2, 7, 6, 1H), 3.92 (s, 2H) (CDCL$_3$) | 314.1$[M]^+$ 209.0$[C_{12}H_{17}N_2CL]^+$ 105.1$[C_7H_5O]^+$ |
| 6 | 4-chloro phenyl | 8.01 (d, J = 7.6, 2H), 7.64 (J = 7.2, 1H) 7.53 (J = 7.6, 2H), 7.22 (d, J = 8.8, 2H) 6.94 (d, J = 8.8, 2H), 3.92 (s, 2H), (CDCL$_3$) | 314.1$[M]^+$ 209.0$[C_{12}H_{17}CLN_2]^+$ 105.1$[C_7H_5O]^+$ |
| 7 | 2, 3-dichloro phenyl | 8.01 (d, J = 7.6, 2H), 7.59 (tt, J = 1.2, 7.6, 1H) 7.53 (J = 7.6, 2H), 7.17-7.13 (m, 2H) 6.97 (dd, J = 5.6, 2.8, 1H), 3.92 (s, 2H) (CDCL$_3$) | 348.3$[M]^+$ 243.2$[C_{12}H_{13}CL_2N_2]^+$ 105.1$[C_7H_5O]^+$ |
| 8 | 4-fluorophenyl | 8.01 (d, J = 7.2, 2H), 7.64 (t, J = 7.2, 1H) 7.53 (t, J = 7.6, 2H), 7.04 (t, J = 8.8, 2H) 6.95-6.93 (m, 2H), 3.92 (s, 2H), (CDCL$_3$) | 298.1$[M]^+$ 193.0$[C_{12}H_{13}FN_2]^+$ 105.1$[C_7H_5O]^+$ |
| 9 | 3-trifluoro methylphenyl | 7.99 (d, J = 7.2, 2H), 7.58 (t, J = 7.6, 1H) 7.43 (J = 7.6, 2H), 7.32 (t, J = 8.0, 1H) 7.14 (br, 1H), 7.04 (d, J = 8.0, 1H) 7.01 (t, J = 7.6, 1H), 4.93 (s, 2H) 3.79-3.14 (br, 3H), (CDCL$_3$) | 348.3$[M]^+$ 243.2$[C_{12}H_{14}F_3N_2]^+$ 105.1$[C_7H_5O]^+$ |
| 10 | 2, 3-dimethyl phenyl | 7.92 (d, J = 7.2, 2H), 7.59 (J = 7.6, 1H) 7.45 (J = 7.6, 2H), 6.94 (J = 7.6, 1H) 6.86 (d, J = 7.6, 1H), 6.82 (d, J = 7.6, 1H) 4.94 (s, 2H), 3.59-3.09 (br, 3H), (CDCL$_3$) | 308.3$[M]^+$ 203.2$[C_{13}H_{19}N_2]^+$ 105.1$[C_7H_5O]^+$ 132.2$[C_9H_{10}N]^+$ |
| 11 | 6-methoxyl-2-benzothiazolyl | 7.92 (d, J = 7.6, 2H), 7.58 (tt, J = 1.2, 7.2, 1H) 7.47 (J = 7.6, 2H), 7.15 (J = 2.4, 1H) 7.45 (s, 1H), 3.90 (s, 2H), 6.90 (dd, J = 2.4, 7.6, 1H), 3.68 ((t, J = 5.2, 4H) 3.82 (s, 2H), (CDCL$_3$) | 367.3$[M]^+$ 262.2$[C_{13}H_{16}N_3OS]^+$ 105.1$[C_7H_5O]^+$ 207.2$[C_{10}H_{11}N_2OS]^+$ |
| 12 | 6-methyl-2-benzothiazolyl | 8.00 (d, J = 7.6, 2H), 7.64 (J = 7.6, 1H) 7.56-7.51 (m, 3H), 7.34 (d, J = 8.4, 1H) 7.08 (dd, J = 0.8, 7.6, 1H), 3.97 (s, 2H) 3.55 (t, J = 1.2, 2H), (CDCL$_3$) | 351.3$[M]^+$ 246.2$[C_{13}H_{16}N_3S]^+$ 105.1$[C_7H_5O]^+$ 191.2$[C_{10}H_{11}N_2S]^+$ |
| 13 | 4-methyl-2-benzothiazolyl | 8.00 (m, 2H), 7.58 (tt, J = 1.2, 7.2, 1H) 7.49-7.43 (m, 3H), 6.98 (t, J = 7.6, 1H) 7.12 (d, J = 7.2, 1H), 3.74 (J = 5.2, 4H) 3.91 (s, 2H), (CDCL$_3$) | 351.3 $[M]^+$ 246.2$[C_{13}H_{16}N_3S]^+$ 105.1$[C_7H_5O]^+$ 191.2$[C_{10}H_{11}N_2S]^+$ |
| 14 | 6-chloro-2-benzothiazolyl | 7.98 (d, J = 7.6, 2H), 7.60 (t, J = 1.2, 7.2, 1H) 7.57 (d, J = 2.0, 1H), 7.48 (t, J = 7.6, 2H) 7.45 (d, J = 8.8, 1H), 7.25 (dd, J = 2.0, 8.8, 1H) 3.97 (s, 2H), (CDCL$_3$) | 371.3$[M]^+$ 266.2$[C_{12}H_{14}CLN_3S]^+$ 105.1$[C_7H_5O]^+$ 211.2$[C_9H_8LN_2S]^+$ |
| 15 | 4-chloro-2-benzothiazolyl | 7.98 (d, J = 7.6, 2H), 7.59 (J = 7.6, 1H) 7.49-7.42 (br, 3H), 7.31 (dd, J = 1.2, 7.6, 1H) 6.98 (t, J = 8.0, 1H), 3.97 (s, 2H) 3.72 (t, J = 5.2, 4H), (CDCL$_3$) | 371.3$[M]^+$ 266.2$[C_{12}H_{14}CLN_3S]^+$ 105.1$[C_7H_5O]^+$ 211.2$[C_9H_8LN_2S]^+$ |
| 16 | 2-pyrimidinyl | 8.51 (d, J = 5.2, 2H), 7.91 (d, J = 7.6, 2H) 7.68 (t, J = 7.6, 2H), 7.51 (t, J = 8.0, 1H) 6.97 (t, J = 5.2, 1H), 5.00 (s, 2H) 4.14-2.89 (br, 8H), (CDCL$_3$) | 282.2$[M]^+$ 177.1$[C_9H_{13}N_4]^+$ 105.1$[C_7H_5O]^+$ |
| 17 | 6-chloro-2-pyridyl | 8.01 (d, J = 7.6, 2H), 7.64 (t, J = 7.6, 1H) 7.53 (t, J = 7.6, 2H), 7.10 (t, J = 8.0, 1H) 6.52 (dd, J = 2.0, 7.6, 1H), 6.44 (t, J = 2.0, 1H) | 315.2$[M]^+$ 210.1$[C_9H_{12}CLN_3]^+$ 105.1$[C_7H_5O]^+$ |

TABLE 1-continued

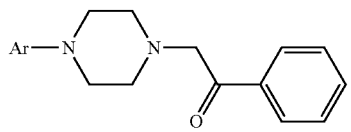

| Example | Ar | HMNR (300 MHz), δ (溶剂) | MS (m/z) |
|---|---|---|---|
| | | 6.36 (dd, J = 2.0, 7.6, 1H), 3.88 (s, 2H), 3, 71 (s, 3H ), (CDCL$_3$) | |

The analgesic activity of the compound of the invention was studied by animal pain models such as HAC writhing test, bee venom stimulating test, hot-plate test and sciatic nerve ligation test with Kuming mice and SD rats.

Experiment Example 1

Acetic Acid-Induced Writhing Test

Kunming mice (18-22 g, male and female each half) were divided into a negative control group, an Aspirin control group, a morphine control group and a group of the compound of the invention. Each group of mice were respectively administered corresponding medicine (0.2 ml/10 g) intragastrically or subcutaneously, The mice of the negative control group were administered, the same volume vehicle. After 60 minutes (intragastrically) or 30 minutes (subcutaneously), each group of mice were administered 0.6% acetic acid solution (0.4 ml) by intraperitoneal injecting, and then writhing times in 15 minutes were observed and recorded immediately. Writhing inhibition rate in mice was used as the pharmacodynamic index of analgesic activity.

Writhing inhibition rate(%)=(writhing times of negative control group−writhing times of medicine group)/Writhing times of negative control group× 100%

$ED_{50}$ values were calculated according to the result. The results are shown in Table 2

TABLE 2

Analgesic activity of the compounds in writhing test

| | $ED_{50}$ (mg/Kg) | |
|---|---|---|
| Sample | intragastrically | subcutaneously (S. C) |
| Example 1 | 20 | 15 |
| Example 2 | 5 | 2 |
| Example 3 | 30 | 20 |
| Example 4 | 80 | 36 |
| Example 5 | 50 | 18 |
| Example 7 | 60 | 20 |
| Example 8 | 120 | 80 |
| Example 9 | 3 | 2 |
| Example 10 | 5 | 10 |
| Example 11 | 200 | 120 |
| Example 12 | 180 | 100 |
| Example 14 | 152 | 78 |
| Example 16 | 132 | 100 |
| Aspirin | 100 | 80 |
| Morphine | 4 | 1 |

The results of Table 2 showed that the compound of the invention can significantly inhibit the writhing times, improve clinical symptoms and have a good analgesic effect.

Experiment Example 2

Hot-Plate Test in Mice

Hot-plate test is one of conventional physiological pain models. Mice lick hind paws, jump up and so on when they are subject to thermal stimulus. Analgesics that take effect on central nervous system can increase the thermo-pain threshold, prolong the latency of protective response.

KM female mice weighting 18-22 g were employed in the test. Primary screening was done before the test to remove the animals whose responses were too slow (>30 s) or too sensitive (<6 s). The mice passing the primary screening were divided into a negative control group, a morphine control group and a group of the compound of the invention. Each group of mice were respectively administered corresponding dose of medicine intragastrically or by intravenous injection, and 60 minutes later, a hot-plate test was done on those mice. The time of first licking hind paws and jumping up was recorded (the data over 60 s is recorded as 60) and compared with the latency of the animals in the control group. The analgesic activity of each dose was calculated and $ED_{50}$ was calculated from the analgesic activity. The results were shown in Table 3.

TABLE 3

Analgesic activity of the compounds in the hot-plate test

| | $ED_{50}$(mg/Kg) | |
|---|---|---|
| Sample | intragastrically | intravenous injection |
| Example 1 | 25 | 8 |
| Example 3 | 50 | 19 |
| Example 5 | 55 | 20 |
| Example 7 | 60 | 20 |
| Example 8 | 120 | 40 |
| Example 9 | 20 | 5 |
| Example 10 | 30 | 10 |
| Example 11 | 150 | 60 |
| Morphine | 2 | 1 |

It can be seen from the results in Table 3 that in the hot-plate test, the compound of formula (I) of the invention showed good analgesic effects.

Experimental Example 3

Bee Venom Test

Adult male Sprague-Dawley (SD) rats weighting 200-250 g were used in the test after acclimation by feeding for 1 week. First, tubes were placed intrathecally (i.t.) in rats. The rats with good conditions after 3-4 days were selected for the bee venom test. The animals were divided into an intrathecal DMSO group, an intrathecal morphine group and a group of intrathecal compounds of the invention. 5 minutes after administration, each group of rats was intravenously injected with 50 μl of bee venom at their left hind limbs. Times of feet spontaneous drawing back every 5 minutes in 60 minutes, as well as total times of feet drawing back in an hour were observed and recorded. The response latency to heat stimulus and threshold of mechanical stimulus on both thenars of each group of rats were measured before intrathecal administration and 2 hours after bee venom injection respectively. The results were shown in Table 4.

TABLE 4

Analgesic activity of the compounds in the bee venom test

| Sample | $ED_{50}$ (μg/Kg) intrathecally |
| --- | --- |
| Example 2 | 100 |
| Example 5 | 60 |
| Example 7 | 80 |
| Example 8 | 120 |
| Example 9 | 20 |
| Example 10 | 30 |
| Example 11 | 200 |
| morphine | 5 |

It can be seen from the results shown in Table 4 that the intrathecal injection of the compound of the invention can significantly reduce the total times of rats' feet spontaneous drawing back ($P<0.05$), and inhibit the spontaneous pain responses induced by bee venom markedly with the inhibition rate of 33.14% and 35.56 respectively. It can be seen from the observation that the effect of easing pain was the best at half an hour after administration; the heat response latency of rats can be prolonged significantly ($P<0.05$); the pain threshold to heat was increased, while no obvious effect was observed on the pain sensitivity to mechanical stimulus.

Experimental Example 4

The Spared Nerve Injury (SNI) Test

Neuropathic pain is also called for short as neuralgia, which is a common chronic pain. It is an abnormal pain condition caused by hurt or disease-induced trauma of peripheral or central nerve, and can not be cured effectively till now. Sciatic nerve branches selective injury model (spared nerve injury, SNI) is a neuralgia model established in 2000 (see Spared nerve injury: an animal model of persistent peripheral neuropathic pain, Pain, 2000 August; 87(2): 149-58). The model can produce reduced robust mechanical allodynia, so it can simulate the clinic nerve pathologic pain relatively well.

Adult male Sprague-Dawley (SD) rats weighting 200-250 g (Experimental Animal Center of Xuzhou Medical College) were employed in the test after acclimation by feeding for 1 week. First, Sciatic nerve branches selective injury model (spared nerve injury, SNI) was replicated, The rats of successful modeling were administered intragastrically on Day 12, 13, 14 after surgery. The mechanical allodynia were measured at 60 minutes after administration every day (von Frey Cilia Apparatus, manufactured by Institute of Biology Bioengineering, Chinese Academy of Medical Science). The results were shown in Table 5.

TABLE 5

Analgesic activity of the compounds in the spared nerve injury (SNI) test

| Sample | $ED_{50}$ (mg/Kg) intragastrically |
| --- | --- |
| Example 1 | 40 |
| Example 2 | 15 |
| Example 3 | 30 |
| Example 4 | 100 |
| Example 5 | 80 |
| Example 7 | 60 |
| Example 8 | 150 |
| Example 9 | 10 |
| Example 10 | 15 |
| Example 11 | 180 |
| Example 12 | 200 |
| Example 14 | 152 |
| Example 16 | 167 |
| Gabapentin | 50 |

It can be seen from the results in Table 5 that the mechanical threshold of each group of rats was reduced significantly on Day 7, indicating that the SNI model can produce mechanical pain sensitivity in rats and the compound of the invention can increase the pain threshold of the rats significantly ($P<0.01$). Therefore, the compound has a better pain-easing effect in such a dose.

What we claim is:

1. A method of treating acute pain, neuropathic pain and/or receptive nociceptive pain in a subject in need thereof comprising administering to the subject a compound, 2-[4-(3-trifluoromethylphenyl)-piperazin-1-yl]-1-acetophenone or a pharmaceutically acceptable salt thereof.

2. The method of claim 1, wherein the compound or a pharmaceutically acceptable salt thereof is administered in combination with another analgesics.

3. The method of claim 1, wherein said subject is human.

* * * * *